United States Patent [19]
Ledl

[11] 3,970,376
[45] July 20, 1976

[54] DEVICE FOR TESTING COLOR VISION

[75] Inventor: Hanne-Lore Ledl, Munich, Germany

[73] Assignee: Optische Werke G. Rodenstock, Germany

[22] Filed: July 11, 1974

[21] Appl. No.: 487,758

[30] Foreign Application Priority Data
July 14, 1973 Germany............................ 2335909

[52] U.S. Cl.................................. 351/35; 351/36; 351/39
[51] Int. Cl.² ....................................... A61B 3/06
[58] Field of Search.......................... 351/35, 36, 39

[56] References Cited
UNITED STATES PATENTS

| | | | |
|---|---|---|---|
| 2,453,335 | 11/1948 | Morris | 351/35 |
| 2,464,001 | 3/1949 | Shepard | 351/39 |
| 3,382,025 | 5/1968 | Knoll | 351/35 X |
| 3,801,188 | 4/1974 | Hunt et al. | 351/35 X |

Primary Examiner—Paul A. Sacher
Attorney, Agent, or Firm—Craig & Antonelli

[57] ABSTRACT

The color vision of a subject to be tested is evaluated by the presentation of a series of test panels having different colors to the subject. Each pair of test panels has prescribed maximum emission values over established wavelength ranges and wavelength values. Depending upon the ability to discern colors of the subject to be tested, the respective pairs of test panels will appear to the subject to have different degrees of color and intensity, so that it can be determined whether or not the color vision of the subject being tested is normal or is protanopic deuteranopic and the degree of the latter color deficiencies can also be evaluated.

8 Claims, 8 Drawing Figures

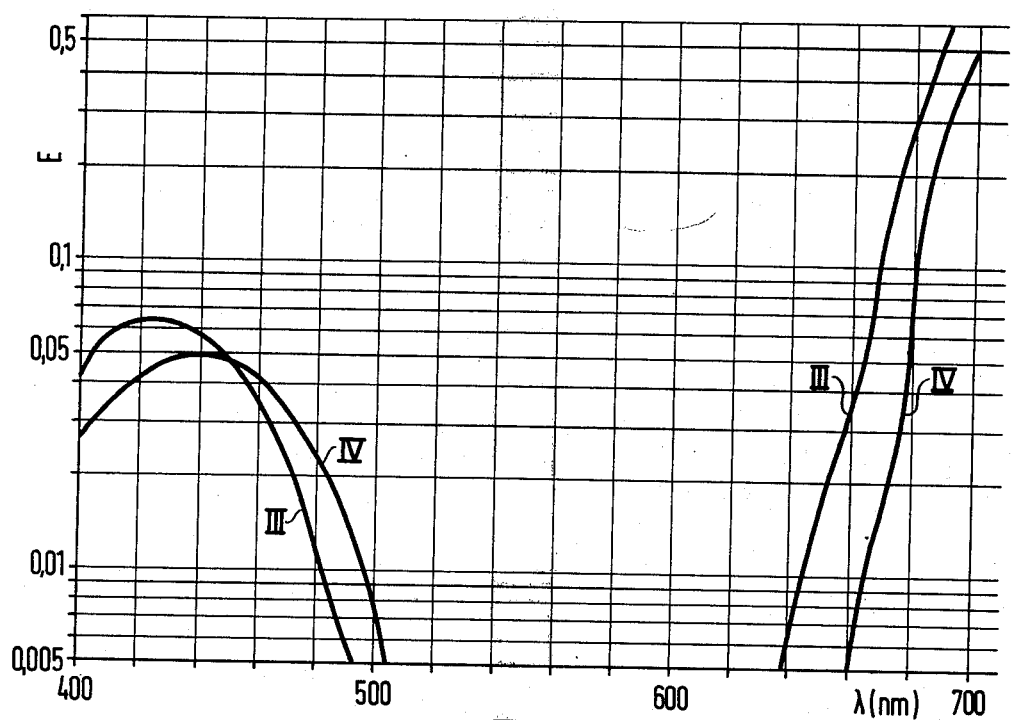
Fig. 3
Fig. 4
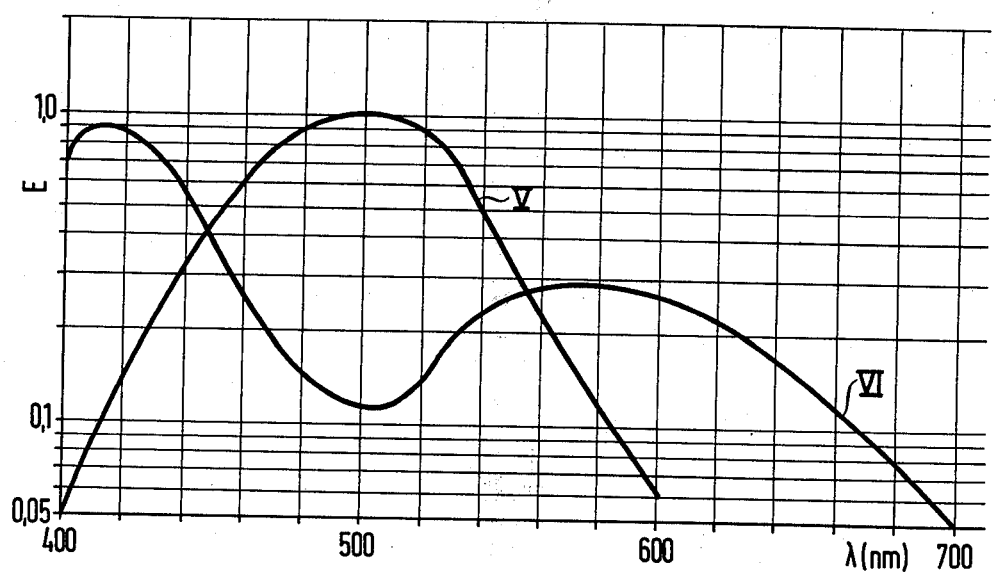

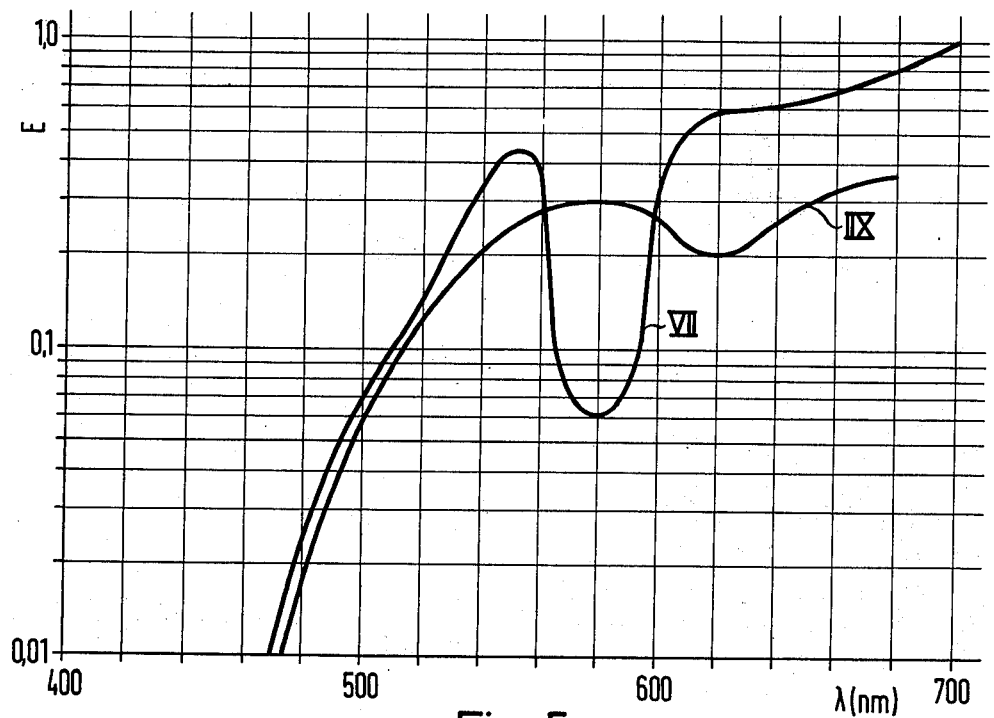
Fig. 5
Fig. 6
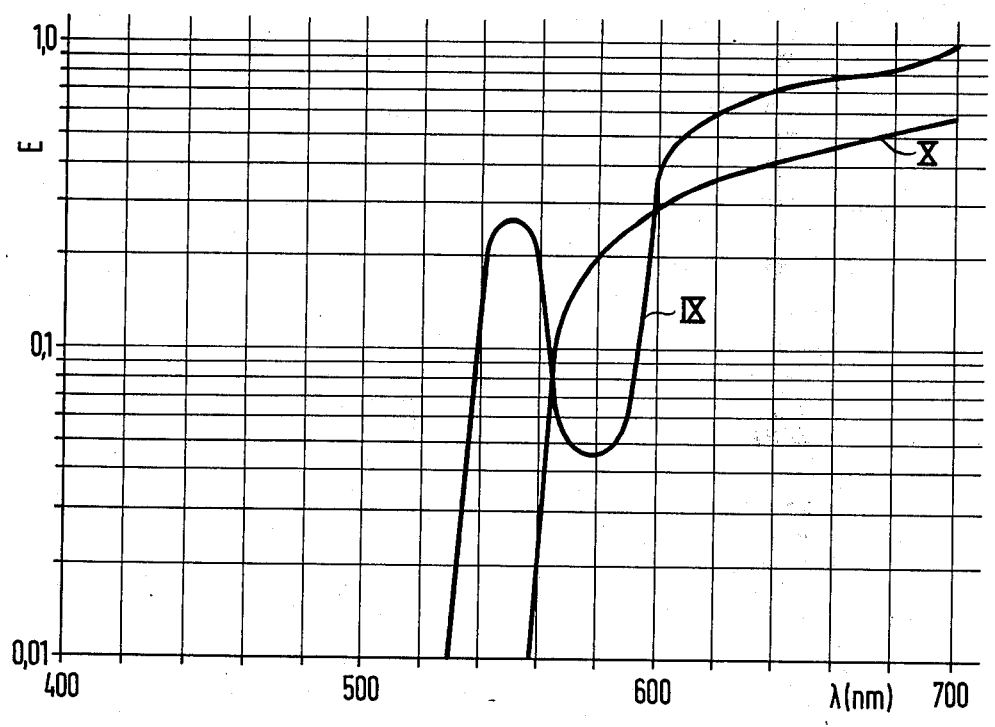

ROTATING DISC

DEVICE FOR TESTING COLOR VISION

BACKGROUND OF THE INVENTION

1. Field of the Invention

The invention relates to an instrument for testing color vision in which a number of test panels of different colors arranged in pairs and transluminated by a light source having a color temperature of approximately 2400°K is presented to the person to be tested.

2. Description of the Prior Art

In the known Nagel anomaloscope, two test areas are presented to the examinee, one test area appearing yellow to the person of normal color vision, emitting a spectral color of approximately 589 nm wavelength having a bandwidth of approximately ± 20 nm. The luminosity of this yellow area is variable by means of a displaceable neutral wedge, and is adjusted to equal the luminosity of the second test panel. The second test panel is of mixed colors constituted by a green spectral color of approximately 546 nm having a bandwidth of approximately ± 20 nm, and a red spectral color of approximately 671 nm having a bandwidth of approximately ± 20 nm. The mixing ratio is continuously variable, and the degree of an existing anomaly in color vision (red-green) can be determined from the extent of deviation from the standard values.

U.S. Pat. No. 2,453,335 describes a test device in which a test area of yellow appearance, the wavelength of the emitted rays ranging between 570 and 600 nm, is to be compared to a test area of mixed color (red-green). The wavelength of the rays emitted by the green color ranges between 520 and 550 nm, the wavelength of the red color being between 650 and 700 nm. In both prior art devices, test panels of yellow spectral color of narrow bandwidth are opposed to test panels having a mixed red-green color, the constitutents of the mixed color being red and green spectral colors of narrow bandwidths.

The examinations by means of these prior art devices are time-consuming and highly complex, and can only be effected by highly specialized personnel. The results of these extensive examination procedures can attain a high degree of precision due to the use of spectral colors of narrow bandwidths. Both devices are not suitable, however, for rapidly conducting mass examinations serving for the purpose of finding out, in a most simple method, whether the person to be examined meets specific minimum requirements regarding color perception, and of determining the nature of existing color vision defects.

BRIEF DESCRIPTION OF THE INVENTION

This problem is solved by the device underlying the present invention in that the first of preferably three pairs of tests panels includes one test area having maximum emission values at wavelengths of 410 and 680 nm, and a second test area with maximum emission values at 440 nm and 680 nm; the second pair of test panels consists of a test area producing maximum emission values at wavelengths of approximately 440 nm and 680nm, and of a test area having the same emission in the blue range, however a more intense emission in the red range at 670 nm; the third pair includes a test area having maximum emission values at 410 nm and 580 nm, and a second test area with a maximum emission at 500 nm.

The invention permits a more precise examination producing results of greater reliability. The bandwidths of spectral emission are selected in such a way that color vision defects can be detected over a wide range.

Pairs of test panels according to the invention can be provided in conventional supporting means, e.g. rotating discs, or slides, in known vision screening devices. They can also be arranged in conventional luminescent cases.

Another arrangement consists in projection to a projection screen by means of a conventional projector. In theory, it is also possible to use color prints for the representation of the individual pairs of test panels; however, the required close tolerances in the reproduction of the colors can hardly be attained by printing techniques.

In a vision screening instrument provided with observation apertures, an equal series of test panels arranged in pairs can be presented to each individual eye of the person to be tested, allowing a separate examination of each eye independently of the fellow eye without the examinee having to change his position relative to the vision screening instrument.

The properties required for the test panels according to the present invention can be attained with a particularly high degree of precision, using color filter glasses of predetermined transmission values. Color modifications due to aging of the components used in the instrument are extremely rare and do not influence the reliability of the tests.

BRIEF DESCRIPTION OF THE DRAWINGS

FIGS. 2 through 6 are illustrations of the emission curves of the individual test panels;

DETAILED DESCRIPTION OF THE INVENTION

Figure 1:
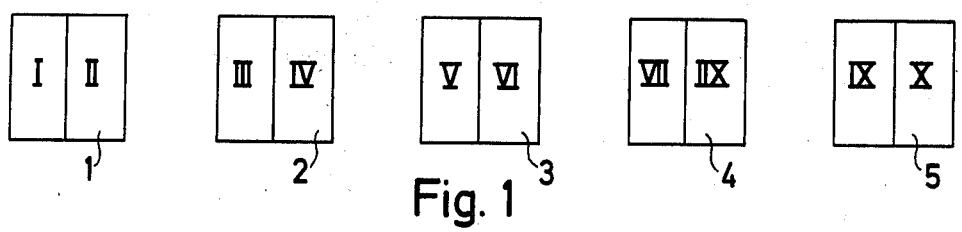
FIG. 1 is a schematic illustration of 5 pairs of test panels.
Figure 2:
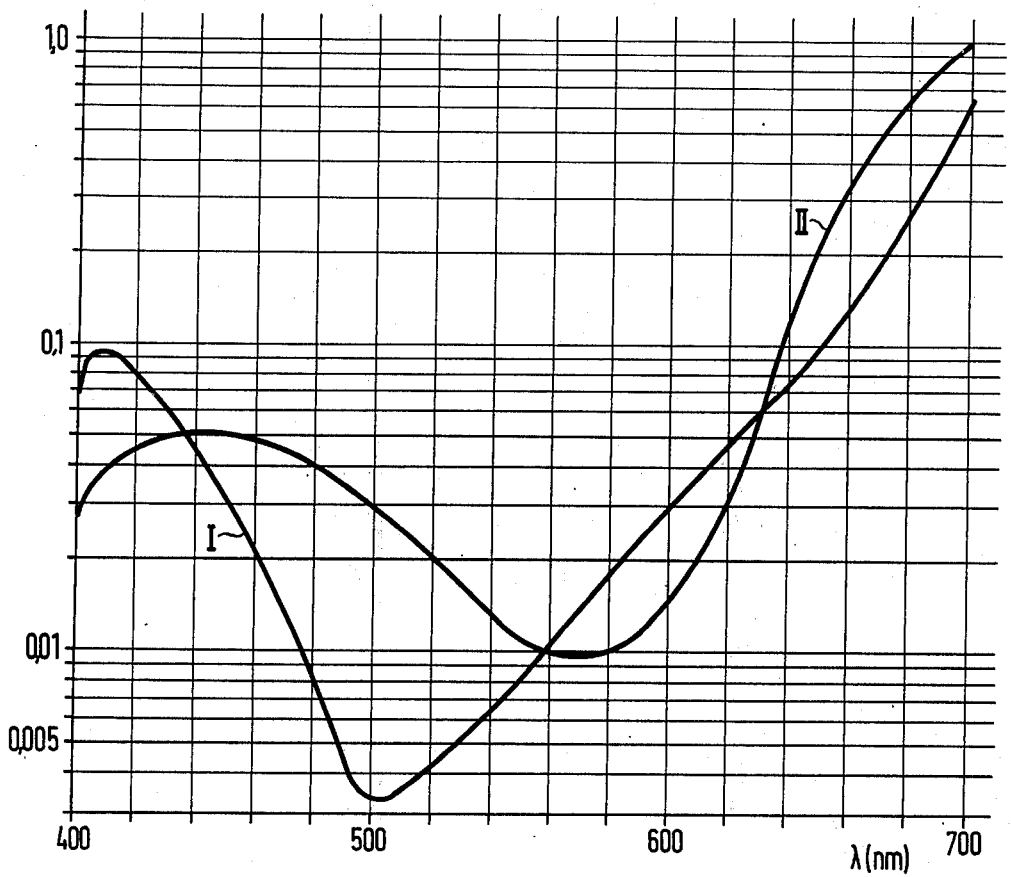
Figure 7:
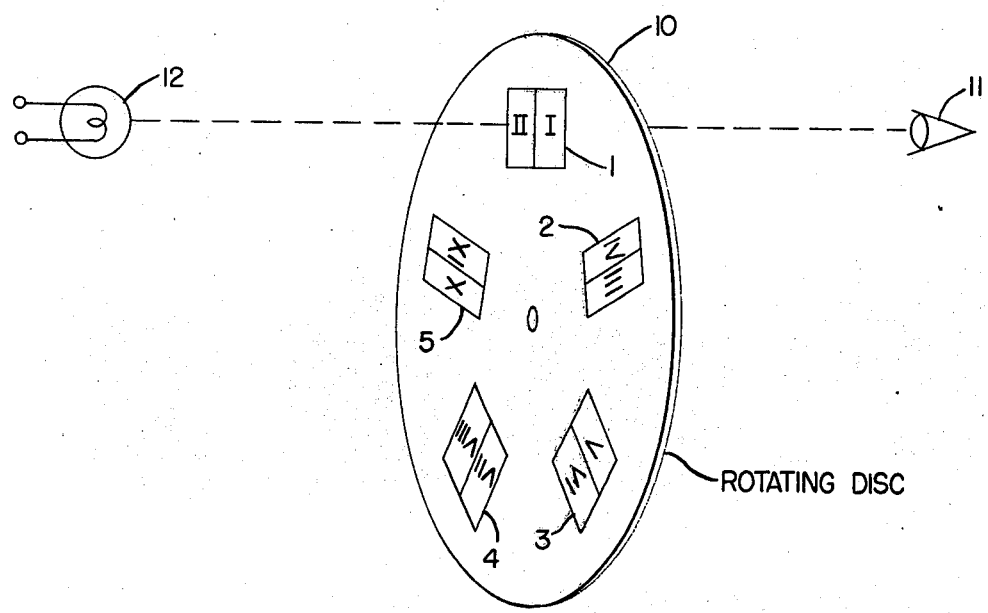
FIG. 7 is an illustration of the manner in which test panels are presented to the eye to be tested.
Figure 8:
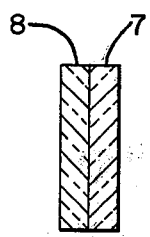
FIG. 8 shows the manner in which plural color glass filters may be employed in the invention.

The pair of test panels 1 comprises the two areas I and II (FIG. 1). The test panels 1 through 5 may be disposed upon a conventional supporting means, for example, a rotating disc 10, as shown in FIG. 7. Light from source 12 illuminates each test pair, so that the test panels may be sequentially presented to each eye 11. The test panels may include a plurality of glass filters 7 and 8, shown in FIG. 8, having respectively different degrees of transmission arranged on top of each other. FIG. 2 shows the transmission characteristics of the two test areas I and II. Both test panels of pair 1 appear to a person of normal color perception as being equal in luminosity and color. The same applies also to persons unable to perceive both red and green colors, as they have a very reduced sensitivity to color differences. To the protanomalous and, in general, also to the deuteranomalous subject, however, the test panels I and II appear unequal, the test area I looking distinctly more reddish to the protanomalous person than test area II. This phenomenon is inverse in case of a deuteranomalous subject.

The optical properties of the pair of test panels No. 2 (FIG. 1) are shown in the curves III and IV of FIG. 3. This pair of test panels appears equal in color and luminosity to the protanopic subject only. On the other hand, the pair of test panels No. 3 (FIG. 1), the characteristic lines of which are shown in FIG. 4 (V and VI), appears only to the deuteranopic subject as being equal in color and luminosity.

The examination result determined by means of the pairs of test panels No. 1 to 3 can be rendered more accurate with the aid of pairs 4 and 5 of test panels (FIG. 1). Since an existing protanopia or deuteranopia can be detected by means of pairs 2 and 3 of test panels, from the patients's answers, pairs 4 and 5 serve for the purpose of distinguishing protanomalous and deuteranomalous subjects from each other, and from the person with normal color perception. Pair 4 of test panels, the characteristic lines of which VII and VIII are shown in FIG. 5, appears equal to the protanomalous subject with the anomalous quotient of approximately 0.3 (according to Nagel). On the other hand, the pair of test panels 5 with its curves IX and X shown in FIG. 6 appears equal to a deuteranomalous person with an anomalous quotient of approximately 4.

By means of these pairs of test panels, it is possible to determine the presence and the kind of a defect in the perception of red and green colors, and whether this visual defect is an anomaly or an anopia.

According to the color emission characteristics of the test panels 1 and 2 shown in FIG. 2, the person of normal color vision perceives both halves as being of equal lilac color and of equal luminosity, whereas the protanopic subject, being unable to perceive the red components, sees two blue colors the hues of which he cannot distinguish i.e., they appear likewise of equal color.

Due to his defect, the deuteranopic subject assesses the left test panel in its spectral composition as being alike to the right half, i.e. he indicates likewise equal color. In contrast to this, the protanomalous subject's ability to perceive red colors is weaker than the normal person's color vision; hence, the left area will appear to him decisively more red than the right half. The deuteranomalous person perceives the left side approximately like a subject with normal color vision; however, his color vision defect may influence the color of the right half in a way that it appears distinctly more red than the left side.

In pair 3 of test panels, the maximum emission values of test area V are at approximately 410 nm and 580 nm, those of test area VI lie at approximately 500 nm. For this reason, they appear different to the protanomalous, the protanopic, and to the person of normal color perception, namely to the latter, test area V appears grey-blue and test area VI, turquoise.

To the deuteranomalous, they have the same appearance, although not such a high contrast, whereas for the deuteranopic, they seem to be equal both in color and luminosity.

For the test areas VII and IX of pairs 4 and 5, a filter combination is provided with emission values at 550 nm and 620 nm. Test panel IIX of pair 4 is designed in such a way that both halves seem to be equal to a protanomalous suffering from an average defect (anomalous quotient approximately 0.3), i.e. it consists in a filter with maximum emission values at 580 nm, appearing pale green to the normal trichromat. Test area X of the pair of test panels 5 is tuned to test area IX in a way that both halves seem to be equal to a deuteranomalous subject. It consists in a filter being transparent only for wavelengths above 560 nm, and showing the hue of a spectral color of approximately 600 nm wavelength. It appears of a dark orange color to the normal trichromat. Test area VII appears pale yellow to a subject of normal color perception, test area IX seems to be pale orange.

While I have shown and described one embodiment in accordance with the present invention it is understood that the same is not limited thereto but is susceptible of numerous changes and modifications as known to a person skilled in the art and I, therefore, do not wish to be limited to the details shown and described herein but intend to cover all such changes and modifications as are obvious to one of ordinary skill in the art.

I claim:

1. In an instrument for testing color vision in which a plurality of pairs of test panels of different colors are presented to a subject to be examined and are illuminated by a light source having a color temperature of about 2400°K, the improvement wherein said pairs of test panels comprise:
   a first pair of panels, a first of which has maximum emission values at wavelengths of 4100 A and 6800 A and a second of which has maximum emission values at 4400 A and 6800 A;
   a second pair of panels, a first of which has maximum emission values at 4400 A and 6800 A and a second of which has a more intense emission in the red range at 6700 A as compared to the first panel of said second pair and has approximately the same maximum emission values as the first panel of the second pair; and
   a third pair of test panels, a first of which has maximum emission values at 4100 A and 5800 A and a second of which has a maximum emission at 5000 A.

2. An improved testing instrument according to claim 1, further comprising:
   a fourth pair of test panels, a first of which has maximum emission values at 5500 A and 6200 A and a second of which has an emission characteristic extending from approximately 5000 A and continuing into the green and red spectral ranges; and
   a fifth pair of test panels, a first of which has maximum emission values at 5500 A and 6200 A, and a second of which has an emission characteristic extending from 5600 A and continuing into the red spectral range.

3. An improved testing instrument according to claim 2, including a supporting carrier on which said pairs of test panels are provided for sequentially presenting said pairs of test panels to the subject to be examined.

4. An improved testing instrument according to claim 3, including means for presenting the same series of pairs of test panels to each eye of the subject to be examined.

5. An improved testing instrument according to claim 3, wherein said test panels include a plurality of glass filters having respectively different degrees of transmission arranged on top of each other.

6. In a method of testing color vision of a subject to be examined wherein test panels of different colors are presented to the subject and are illuminated by a light source having a color temperature of about 2400°K, the improvement comprising the steps of:
   a. sequentially presenting to the subject plural pairs of test panels respectively including
      a first pair of panels, a first of which has maximum emission values at wavelengths of 4100 A and 6800 A and a second of which has maximum emission values at 4400 A and 6800 A;
      a second pair of panels, a first of which has maximum emission values at 4400 A and 6800 A and a second of which has a more intense emission in the red range at 6700 A as compared to the first panel of said second pair and has approximately the same maximum emission values as the first panel of the second pair;

a third pair of test panels, a first of which has maximum emission values at 4100 A and 5800 A and a second of which has a maximum emission at 5000 A;

b. evaluating the degree of an existing anomaly in the color vision of the subject in accordance with the response of the subject to the respective sequential viewing presentation of said pairs of panels.

7. The improvement according to claim 6, wherein the plural pairs of test panels presented to the subject in step (a) include:

a fourth pair of test panels, a first of which has maximum emission values at 5500 A and 6200 A and a second of which has an emission characteristic extending from approximately 5000 A and continuing into the green and red spectral ranges; and a fifth pair of test panels, a first of which has maximum emission values at 5500 A and 6200 A, and a second of which has an emission characteristic extending from 5600 A and continuing into the red spectral range.

8. The improvement according to claim 7, wherein the same series of pairs of test panels are presented to each eye of the subject to be examined.

* * * * *